United States Patent [19]

Nishioka et al.

[11] Patent Number: 4,621,284
[45] Date of Patent: Nov. 4, 1986

[54] MEASURING ENDOSCOPE

[75] Inventors: Kimihiko Nishioka; Hiroyoshi Fujimori, both of Hachiouji, Japan

[73] Assignee: Olympus Optical Co., Ltd., Tokyo, Japan

[21] Appl. No.: 742,056

[22] Filed: Jun. 6, 1985

[30] Foreign Application Priority Data

Jun. 9, 1984 [JP] Japan .................................. 59-118836

[51] Int. Cl.⁴ .......................... A61B 1/06; H04N 7/18
[52] U.S. Cl. .......................................... 358/98; 128/6; 358/1; 358/107
[58] Field of Search ............................ 358/98, 107, 1; 128/4-11

[56] References Cited

U.S. PATENT DOCUMENTS

| 4,039,829 | 8/1977 | Kato | 358/107 |
| 4,261,344 | 4/1981 | Moore | 358/98 |
| 4,331,132 | 5/1982 | Mukasa | 358/98 |
| 4,558,691 | 12/1985 | Okada | 128/6 |

FOREIGN PATENT DOCUMENTS

58-67230 4/1983 Japan .
59-70908 4/1984 Japan .

Primary Examiner—Howard W. Britton
Attorney, Agent, or Firm—Cushman, Darby & Cushman

[57] ABSTRACT

A measuring endoscope comprising an observing light projecting means, a measuring light projecting means, a single image pickup optical system, an observing image signal processing means, a measuring image signal processing means and a color displaying means, and arranged so that the observing and measuring image are picked up as divided in the time, the observing image signal is stored in a memory so that, in the measuring image pickup period, the observing image signal stored in the memory will be put into the color displaying means to continuously display the normal observing image on the displaying means, in order to make so that the means to be used for the measurement do not obstruct the normal observation.

8 Claims, 16 Drawing Figures

MEASURING ENDOSCOPE

BACKGROUND OF THE INVENTION (a) Field of the Invention

This invention relates to a measuring endoscope whereby such information as the size and irregularities of an object to be observed can be obtained.

(b) Description of the Prior Art:

Such measuring endoscope as of this kind is already known, for example, from Japanese Patent Preliminary Publication No. Sho 58-67230. In this known measuring endoscope, two semiconductor lasers are arranged around an observing optical system to project two spot images onto an object to be observed parallelly with the optical axis of the observing optical system from these semiconductor lasers to measure the size of the object on the basis of the distance between these spot images. However, in this system, as the spot images will overlap on the image of the object even at the time of the normal observation, there has been a defect that, in the case of the normal observation, the spot images will obstruct the observation.

SUMMARY OF THE INVENTION

Therefore, a primary object of the present invention is to provide a measuring endoscope wherein the means to be used for the measurement will not obstruct the normal observation.

According to the present invention, this object is attained by a formation wherein the observing image and measuring image are picked up as devided in the time, the observing image signal is stored in a memory so that, in the measuring image pickup period, the observing image signal stored in the memory will be put into a monitor or the like to continuously display the normal observing image.

This and other objects of the present invention will become more apparent during the course of the following detailed description and appended claims.

DESCRIPTION OF THE PREFERRED EMBODIMENTS

Figure 1:
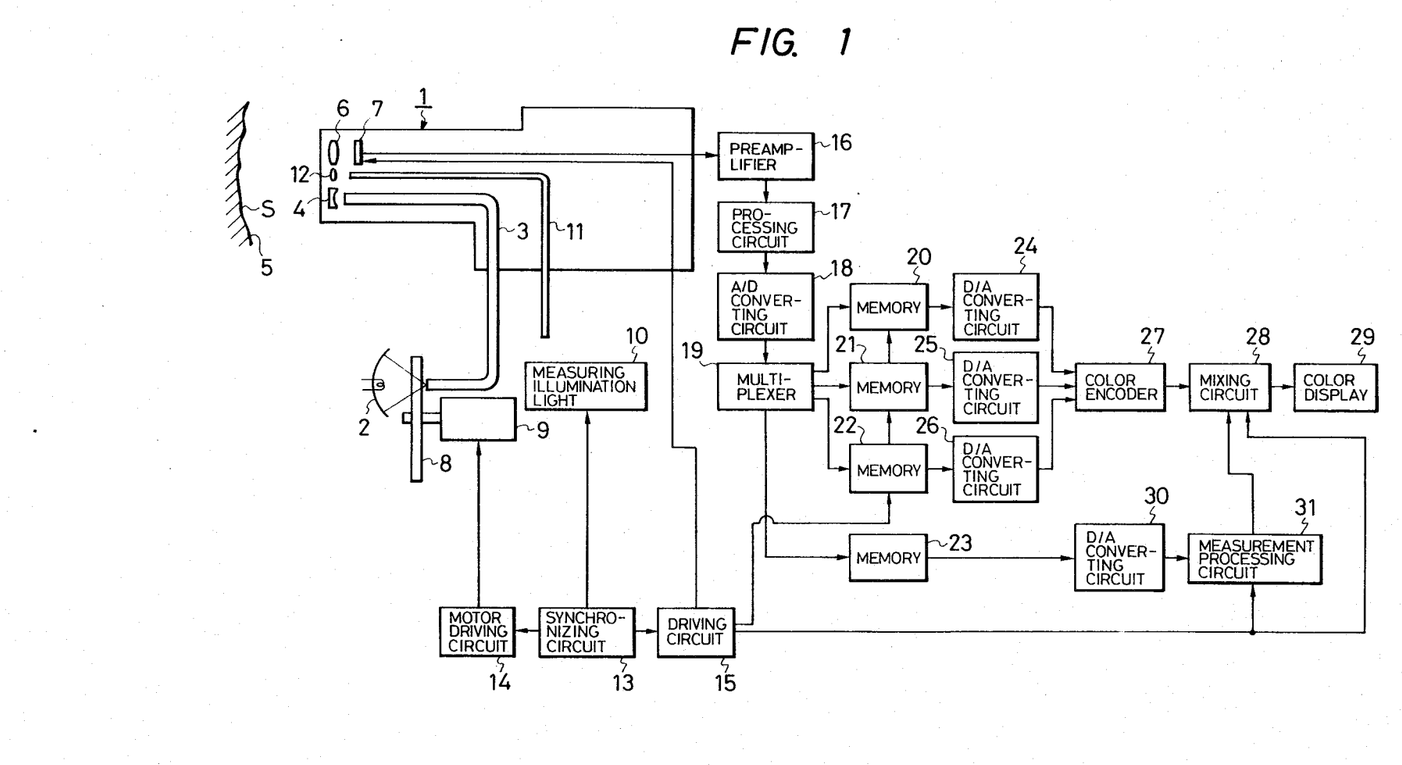
FIG. 1 is a schematic view of an embodiment of the endoscope according to the present invention.
Figure 2:
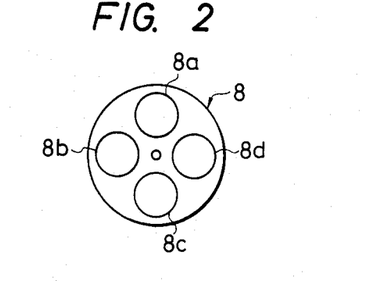
FIG. 2 is an elevational view of a rotary filter in FIG. 1.

The present invention shall be explained in the following on the basis of the embodiments shown in the drawings. In FIG. 1, the reference numeral 1 represents an endoscope body, 2 represents an observing illumination light source, 3 represents an observing light guide, 4 represents an observing illumination lens, 5 represents an object to be observed, 6 represents an objective lens, 7 represents such solid-state image sensor as CCD, 8 represents a rotary filter arranged rotatably by a motor 9 between the illumination light source 2 and light guide 3 and consisting as shown in FIG. 2 of a red light transmitting portion 8a, green light transmitting portion 8b, blue light transmitting portion 8c and light interrupting portion 8d, 10 represents a measuring illumination light source, 11 represents a measuring light guide and 12 represents a measuring light projecting lens. The reference numeral 13 represents a synchronizing circuit, 14 represents a motor driving circuit to drive the motor 9 rotating the rotary filter 8 on the basis of a control signal from the synchronous circuit 13, 15 represents a driving circuit to operate the solid-state image sensor 7 on the basis of the control signal from the synchronous circuit 13, 16 represents a pre-amplifier to amplify the output signal of the solid-state image sensor, 17 represents a processing circuit, 18 represents an A/D converting circuit, 19 represents a multiplexer, 20 to 23 represent respective memories into which signals corresponding to illuminations by a red light, green light, blue light and measuring light as synchronized with the rotation of the rotary filter 8 are put as divided by the multiplexer 19, 24 to 26 represent D/A converting circuits, 27 represents a color encoder, 28 represents a mixing circuit, 29 represents a color display used as a monitor, 30 represnets a D/A converting circuit 31 represents a measurement processing circuit for processing the signal stored in the memory 23.

Figure 3:
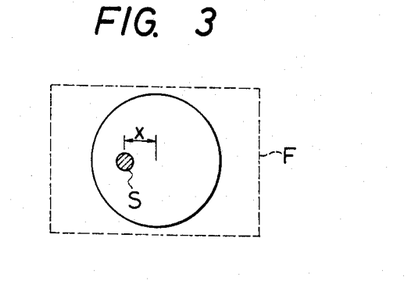
FIG. 3 is a view showing a spot illumination within the observing visual field.

As the embodiment of the presnet invention is formed as in the above, the light coming out of the observing illumination light source 2 will be converted in turn to a red light, green light, blue light and dark by the rotation of the rotary filter 8 by the motor 9 to illuminate the object 5 through the light guide 3 and illuminating lens 4. However, when the light interrupting portion 8d of the rotary filter 8 is inserted in the light path, on the basis of the control signal from the synchronizing circuit 13, a light will be emitted out of the measuring illumination light sourse 10 and will spot-illuminate the object 5 within the image pickup visual field F as shown, for example, by S in FIG. 3 through the light guide 11 and measuring light projecting lens 12. The image of the thus illuminated object 5 to be observed will be formed on the solid-state image sensor 7 by the objective lens 6. The solid-state image sensor 7 will be operated by the driving circuit 15 as synchronized with the rotation of the rotary filter 8 on the basis of the control signal from the synchronizing circuit 13, the respective signals of the object image by the red light, green light, blue light and measuring light will be put out in turn, will be amplified by the pre-amplifier 16, will be processed by the processing circuit 17, then will be converted to digital signals by the A/D converting circuit 18 and will be divided into the respective memories 20 to 23 by the multiplexer 19. That is to say, there will be respectively put and stored the image signal by the red light into the memory 20, the image signal by the green light into the memory 21, the image signal by the blue light into the memory 22 and the image signal by the measuring light into the memory 23. The digital image signals by the red light, green light and blue light stored in the respective memories 20, 21 and 22 will be simultaneously read out by the reading-out pulses from the driving circuit 15, will be respectively converted to analogue signals by the D/A converting circuits 24, 25 and 26 and will be fed to the color encoder 27 to produce a video signal. This video signal will be further fed to the mixing circuit 28, will here have the synchronous signal from the synchronizing circuit 13 added to it through the driving circuit 15 so as to be a composite video signal and will be indicated as a color video image on the color display 29. The image signal by the measuring light stored in the memory 23 will be converted to an anologue signal by the D/A converting circuit 30, will be processed for such predetermined measurement as, for example, of the distance to the object 5 by the measurement processing circuit 31, then will be converted to a composite video signal by the mixing circuit 28 and will be indicated as measurement data on the right below the color image on the color display 29 as shown, for example, in FIG. 5.

Figure 4:
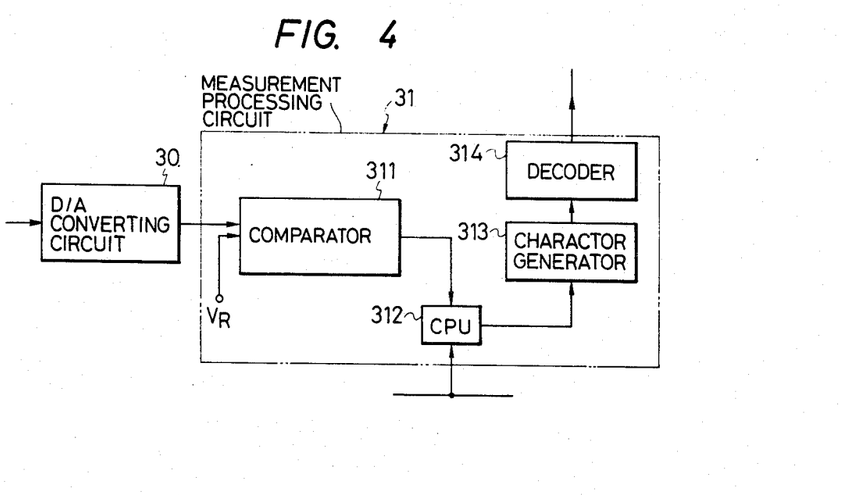
FIG. 4 is a detailed view showing an embodiment of a measurement processing circuit in FIG. 1.
Figure 5:
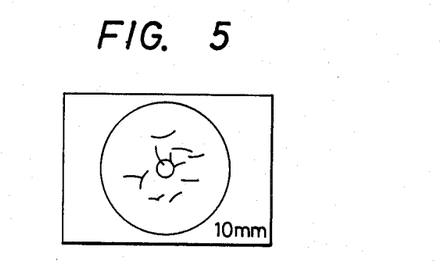
FIG. 5 is a view showing an example of indicating measured data.

Here, an embodiment of the measurement processing circuit 31 in the case of measuring the distance from the tip of the endoscope body 1 to the object 5 as a measurement processing shall be explained more particularly with reference to FIG. 4. In FIG. 4, the reference numeral 311 represents a comparator, 312 represents a CPU, 313 represents a character generator, 314 represents a decoder and the reference symbol $V_R$ represents a reference voltage. As described above, the signal stored in the memory 23 will be converted to an anologue signal by the D/A converter 30 and then will be fed to the comparator 311 through one terminal. The reference voltage $V_R$ applied to the other terminal of the comparator 311 has the value selected to remove the dark current component so that, only in case a signal higher than a predetermined level (for example, the signal representing the spot S in FIG. 3) in put into the above mentioned one terminal, the comparator 311 will operate. Thus, when the above mentioned video signal by the measuring light is fed to the comparator 311, a signal will appear at its output end and this operating signal will be fed to the CPU 312. On the other hand, as a reading-out pulse is fed to the CPU 312 from the driving circuit 15, by these two input signals, the CPU 312 will judge from what numberth picture element forming the solid-state image sensor 7 the signal indicating the spot S is obtained and will send out to the character generator 313 a predetermined address signal on the basis of the result of the judgment. The character generator 313 will put out a character signal in response to the designated address and this signal will be converted to a video signal by the decoder 314 and will be mixed with the video signal based on the observing image signal to appear as a character as shown in FIG. 5. In order to improve the measuring precision, the light guide 11 and lens 12 had better be separate from the lens 6 and solid-state image sensor 7. In this case, the distance X of the measuring spot S from the visual field center of the image shown in FIG. 3 will vary with the distance from the tip of the endoscope to the object 5 on the basis of the parallax between the image optical system and measuring illumination optical system, therefore the distance X of the image of the measuring spot S from the visual field center of the image will be determined from the image signal by the measuring light stored in the memory 23 in the measurement processing circuit 31 and the distance from the tip of the endoscope to the object 5 will be determined on the basis of the picture angle and magnification of the objective lens 6 put into the memory 23 as data in advance. Thus, the normal observation and measurement will be made in parallel in each period by making the four fields of the illumination by the red light, green light, blue light and measuring light one period and therefore, the normal observation will be able to be continuously made without being obstructed by the measurement simultaneously with various measurements of the object to be observed. By the way, the measurement data obtained in the measurement processing circuit 31 can be indicated on a color display not illustrated separately from the observation through another mixing circuit than the mixing circuit 28. The normal image to be observed and the image by the spot illumination may be indicated as overlapped on the above mentioned color display not illustrated. In the above described embodiment, one TV picture is formed of by picking up the image four times and therefore the signal from the solid-state image sensor must be read out at a speed four times the time required to form one TV picture.

As evident from the above explanation, the preamplifier 16, processing circuit 17, A/D converting circuit 18, multiplexer 19, memories 20, 21 and 22, D/A converting circuits 24, 25 and 26, color encoder 27 and mixing circuit 28 form an observing image processing means and the preamplifier 16, processing circuit 17, A/D converter 18, multiplexer 19, memory 23, D/A converting circuit 30, measurement processing circuit 31 and mixing circuit 28 form a measuring image processing means.

Figure 6:
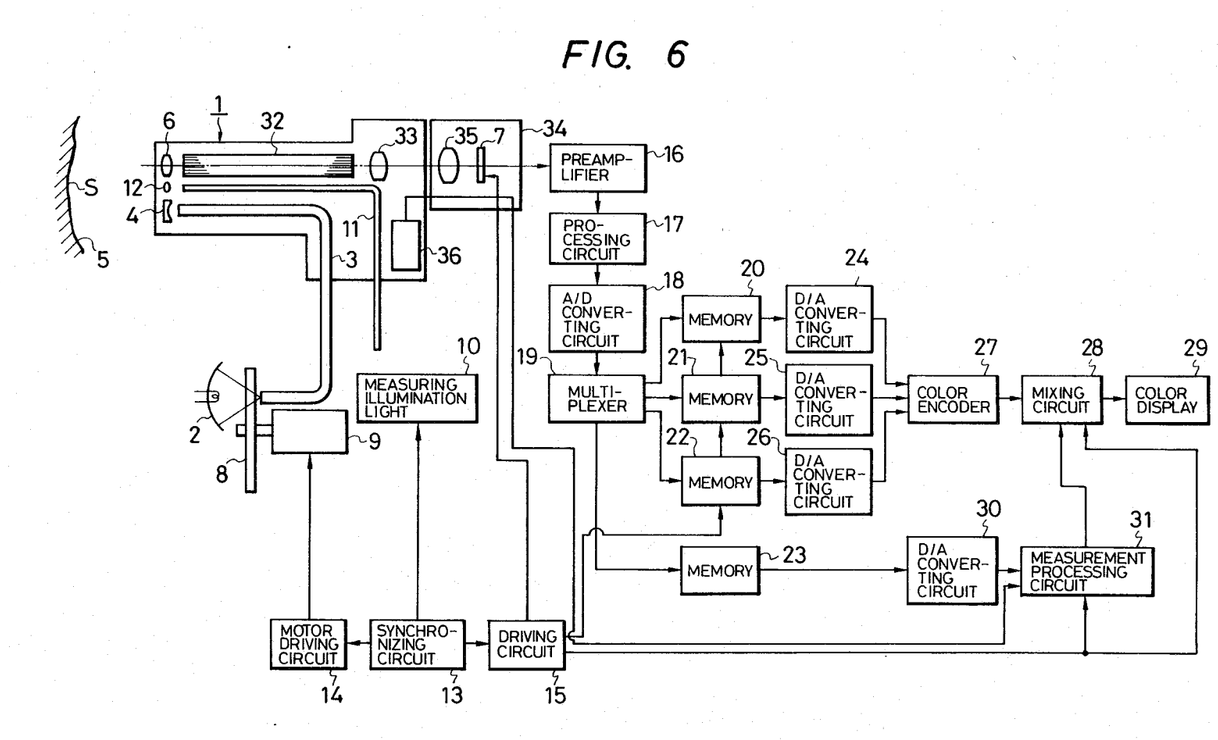
FIG. 6 is a schematic view showing a modification of FIG. 1.

FIG. 6 shows a modification of the embodiment shown in FIG. 1. The formation and operation are the same as in the embodiment in FIG. 1 except that the image of the object 5 to be observed will be formed on the solid-state image sensor built-in within the TV camera 34 through the normal observing optical system formed of the objective lens 6, image guide 32 and eyepiece 33 and through the image forming lens 35 of the TV camera fitted in the rear of the observing optical system. By the way, the reference numeral 36 represents a memory which is built-in within the endoscope body 1 and preferably can be connected by fitting the TV camera 34 to the endoscope body 1 and in which such data of the distance between the observing optical axis and measuring illumination optical axis and the angle of view and magnification of the objective lens 6 as are required for the measurement processing so that, when the TV camera 34 is fitted, these data will be automatically fed to the measurement processing circuit 31.

Figures 7, 8:
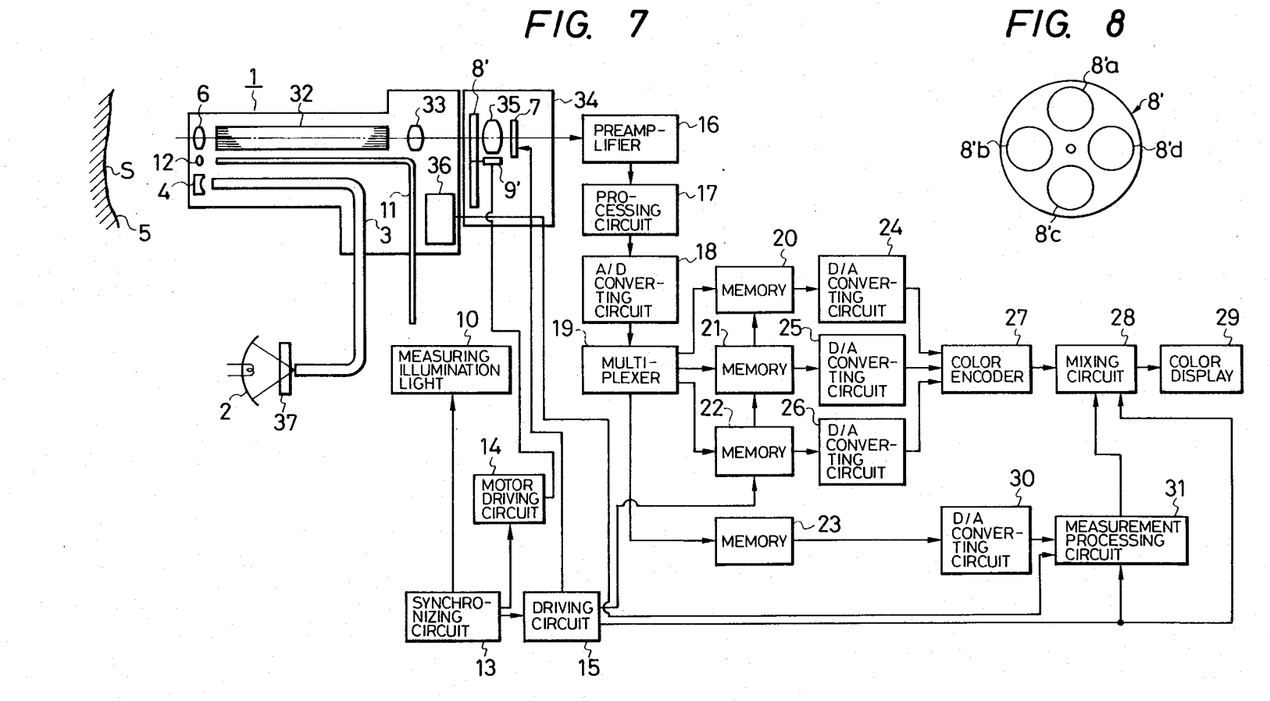
FIG. 7 is a schematic view showing another modification of FIG. 1.
FIG. 8 is an elevational view of a rotary filter in FIG. 7.

FIG. 7 shows a modification wherein a rotary filter 8' arranged in front of the image forming lens 35 of the TV camera 34 so as to be rotated by a motor 9' controlled by the driving circuit 14 and consisting of a red light transmitting portion 8'a, green light transmitting portion 8'b, blue light transmitting portion 8'c and infrared light transmitting portion 8'd as shown in FIG. 8 is provided instead of the rotary filter 8 in the embodiment in FIG. 6, an infrared ray cutting filter 37 is provided between the observing illumination light source 2 and light guide 3 and the measuring illumination light source 10 is formed as a light source emitting an infrared light. According to this formation, the illuminating light sources 2 and 10 may be always emitting lights, in case the light transmitting portion 8'a, 8'b or 8'c of the rotary filter 8' is inserted in the light path, the object 5 illuminated by the illuminating light source 2 will form an image on the solid-state image sensor 7, in case the infrared light transmitting portion 8'd of the rotary filter 8' is inserted in the light path, the object 5 spot-illuminated by the infrared light from the measuring illumination light source 10 will form an image on the solid-state image sensor 7 and thereafter the output signal from the solid-state image sensor 7 will be processed the same as in the embodiment in FIG. 1.

Figure 9:
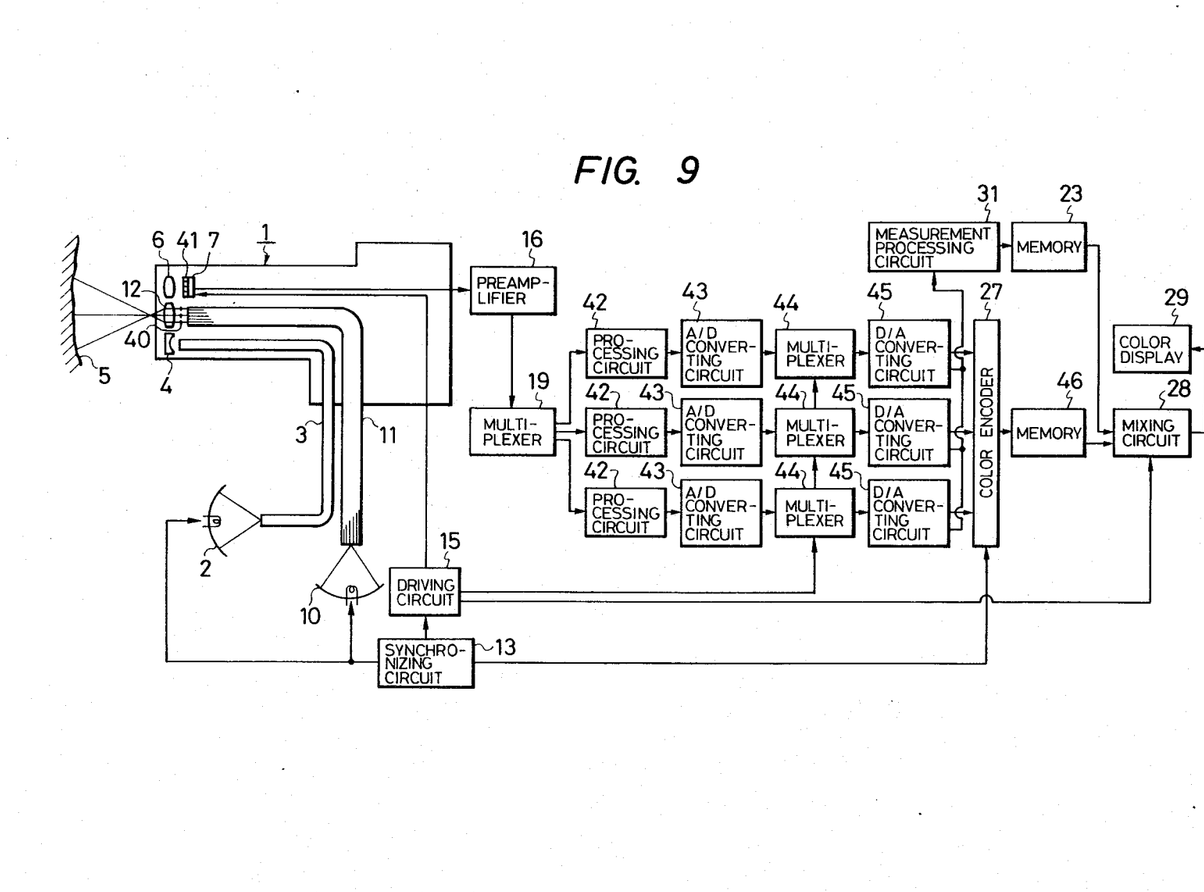
FIG. 9 is a schematic view showing a second embodiment of the present invention.
Figure 10A:
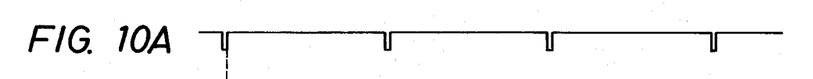
FIGS. 10A through 10E are time charts for the light emission of the light source and reading out the object image and solid-state image sensor in FIG. 9.
Figure 10B:
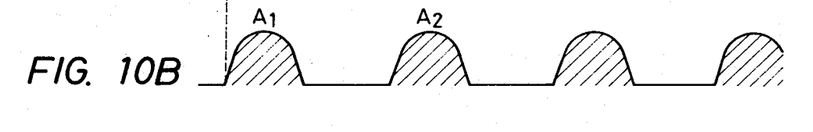
Figure 10C:
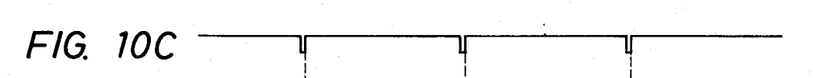
Figure 10D:
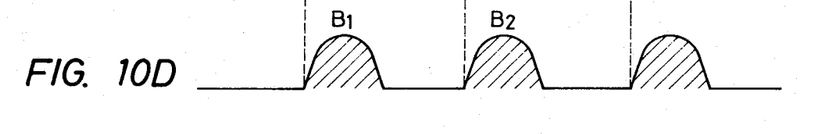
Figure 10E:
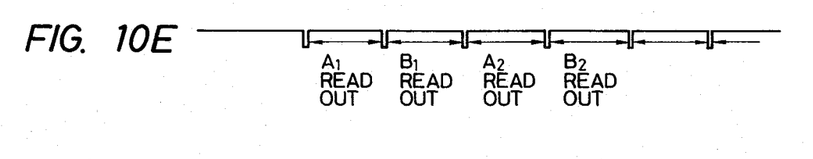

FIG. 9 shows a second embodiment of the present invention. The reference numeral 40 represents a grate pattern arranged between the exit end of the measuring light guide 11 and image projecting lens 12 and provided with light interrupting portions made by grate lines or minute specks regularly arranged in the form of a grate on such transparent plate as, for example, of glass (or provided with light transmitting portions in such form on an opaque plate), 41 represents a color encoding filter provided in front of the solid-state image sensor 7, 42 represents processing circuits provided for the respective colors, 43 represents A/D converting circuits, 44 represents multiplexers, 45 represents D/A converting circuits and 46 represents a memory. The illuminating light sources 2 and 10 are made to alternately emit lights as in FIGS. 10B and 10D by control signals (as shown in FIGS. 10A and 10C) from the synchronizing circuit 13. That is to say the illuminating light source 2 will emit light as shown by $A_1$, $A_2$, ... in FIG. 10B and the illuminating light source 10 will emit light as shown by $B_1$, $B_2$... in FIG. 10D. The image of the object 5 uniformly illuminated by the intermittent light emitted from the illuminating light source 2 or the image of the object 5 on which the grate pattern is projected by the intermittent light emitted from the illuminating light source 10 will be formed on the solid-state image sensor 7, the solid-state image sensor 7 will read out the respective images $A_1$, $B_1$, $A_2$, $B_2$, ... as in FIG. 10E as synchronized with the respective emitted lights on the basis of the control signal from the synchronizing circuit 13, the output signal from the solid-state image sensor 7 will be amplified by the preamplifier 16, will be devided into image signals by the red light, green light, green light and blue light by the multiplexer 19, will be processed by the respective processing circuits 42 and will be converted to digital signals by the respective A/D converting circuits 43 and then the signals $A_1$, $A_2$, ... by the illuminating light source 2 will be converted to video signals by the color encoder 27 through the multiplexer 44 and D/A converting circuit 45 and will be put into the memory 46. The signals $B_1$, $B_2$, ... by the illumination light source 10 will be converted to analogue signals by the D/A converting circuit 45, will then be fed to the measurement processing circuit 31 to have such various measurements as of the irregularities of the surface of the object 5 processed on the basis of the distortion of the grate pattern image projected on the object 5 or to have data processed and then will be put into the memory 23. Thus the observing video signal stored in the memory 46 and measuring video signal stored in the memory 23 will be simultaneously fed to the mixing circuit 28 so as to be a composite video signal by adding the synchronizing signal from the driving circuit 15 and will be indicated simultaneously on the color display 29. In such case, the observing video signal will be picked up at intervals of one field, therefore one signal stored in the memory 46 will indicate two fields and the normal observing image will be continuously indicated.

Figure 11:
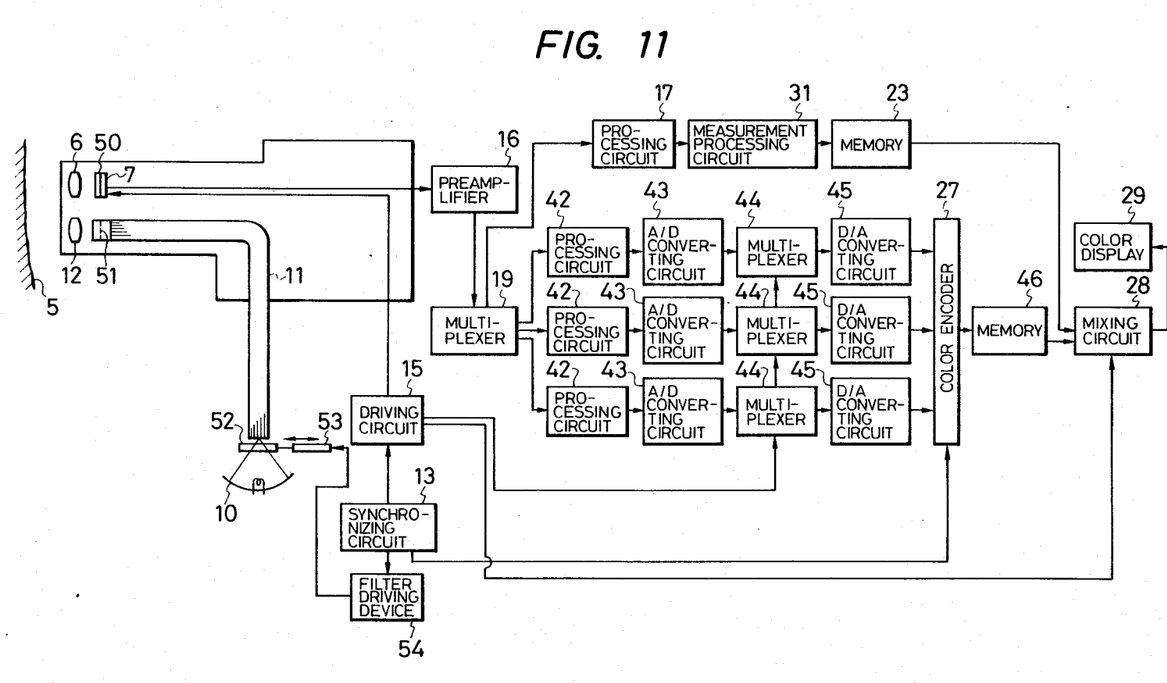
FIG. 11 is a schematic view showing a modification of FIG. 9.
Figure 12:
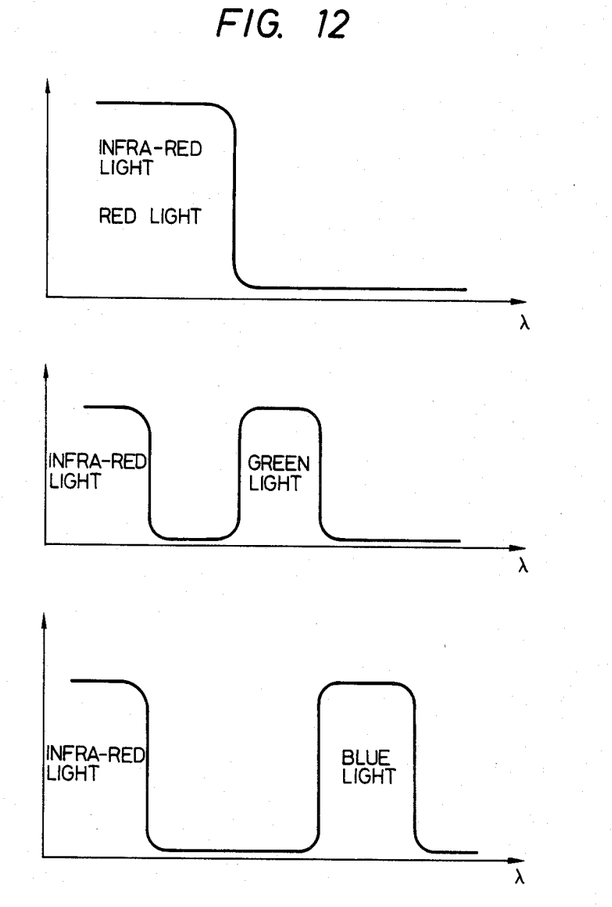
FIG. 12 is a graph showing the transmissibility characteristics of a mosaic filter in FIG. 11.

FIG. 11 shows a modification of the embodiment in FIG. 9. The reference numeral 50 indicated a color encoading mosaic filter provided in front of the solid-state image sensor 7. Its respective picture elements have such transmission factor characteristics as are shown in FIG. 12, transmitting an infrared light together with a red, green or blue light. The reference numeral 51 represents a measuring pattern provided at the exit end of the light guide 11 to transmit a visible light and absorb or reflect an infrared light, 52 represents an infrared ray cutting filter, 53 represents a filter absorbing or reflecting a visible light and transmitting an infrared light and 54 represents a filter driving device for selectively inserting the filters 52 and 53 into the light path and operating on the basis of the control signal from the synchronizing circuit 13. When the filter 52 is inserted in the light path, a visible light will illuminate the object 5 through the light guide 11, measuring pattern 51 and illuminating lens 12, thus the object image formed on the solid-state image sensor 7 will include the color signals encoded by the mosaic filter 50, the output signal from the solid-state image sensor 7 will be amplified by the preamplifier 16, will be divided into image signals by the red, green and blue lights by the multiplexer 19, will be processed the same as is explained with reference to FIG. 9 and will be put into the memory 46. When the filter 53 is inserted in the light path, the image of the measuring pattern 51 will be projected onto the object 5 by the infrared light and the image signal of the object image thus formed on the solid-state image sensor 7 will be amplified by the preamplifier 16, will be put into the processing circuit 17 to be processed, will then have various measurements or data processed by the measurement processing circuit 31 and will be put into the memory 23. The video signals stored in the memories 23 and 46 will be made a composite video signal by the mixing circuit 28 and will be indicated on the color display 29.

As described above, according to the presnet invention, the observing image and measuring image are picked up as devided in the time, the observing image signal is stored in the memory and, during the measuring image pickup period, the observing image signal stored in the memory is put into the monitor or the like so that the normal observing image may be continuously indicated. Therefore, there is obtained a very effective measuring endoscope wherein the observation will not be obstructed by various measurements in the case of making the normal observation.

By the way, the principle of the present invention has been described as applied to the endoscope in the above explanation but can be applied not only to it by also to optical instruments for making any other kinds of measurements.

What is claimed is:

1. A measuring endoscope comprising an observing light projecting means, a measuring light projecting means arranged adjacently to said observing light projecting means, a single image pickup optical system for picking up the image of an object illuminated by said observing light projecting means and measuring light projecting means, an observing image signal processing means connected to said image pickup optical system and having a memory therein to process the observing image signal obtained by said image pickup optical system, a measuring image signal processing means connected to said image pickup optical system to process the measuring image signal obtained by said image pickup optical system and a displaying means connected to said observing image signal processing means and measuring image signal processing means, whereby the observing image and measuring image are picked up as divided in the time and the observing image signal is stored in said memory so that, during the measuring image pickup period, the observing image signal stored in the memory is put into said displaying means to be continuously indicated by said displaying means.

2. A measuring endoscope according to claim 1 wherein said observing light projecting means comprises an observing light source, a rotary filter arranged adjacently to said observing light source and having a red light transmitting portion, green light transmitting portion, blue light transmitting portion and light interrupting portion and a light guide leading the light transmitted through said rotary filter to the object, said measuring light projecting means comprises a measuring light source lighted only while the light from said observing light source is interrupted by said rotary filter and a light guide leading the light from said measuring light source to the object and said image pickup optical system comprises a solid-state image sensor.

3. A measuring endoscope according to claim 1 wherein said observing light projecting means comprises an observing light source, a rotary filter arranged adjacently to said observing light source and having a red light transmitting portion, green light transmitting portion, blue light transmitting portion and light interrupting portion and a light guide leading the light transmitted through said rotary filter to the object, said measuring light projecting means comprises a measuring light source lighted only whily the light from said observing light source is interrupted by said rotary filter and a light guide leading the light from said measuring light source to the object and said image pickup optical system comprises an image guide and a TV camera fitted to the exit side of said image guide.

4. A measuring endoscope according to claim 1 further comprising a memory automatically feeding data necessary for the measurement processing to said measuring image processing means when said TV camera is fitted.

5. A measuring endoscope according to claim 1 wherein said observing light projecting means comprises an observing light source, an infrared ray cutting filter arranged adjacently to said observing light source and a light guide leading the light from said observing light source transmitted through said infrared ray cutting filter onto the object, said measuring light projecting means comprises a measuring light source emitting an infrared light and a light guide leading the infrared light onto the object and said image pickup optical system comprises an image guide and a TV camera fitted to the exit side of said image guide and containing a rotary filter having a red light transmitting portion, green light transmitting portion, blue light transmitting portion and infrared light transmitting portion.

6. A measuring endoscope according to claim 5 further comprising a memory automatically feeding data necessary for the measurement processing to said measuring image processing means when said TV camera is fitted.

7. A measuring endoscope according to claim 1 wherein said observing light projecting means comprises an observing light source lighted at predetermined intervals and a light guide leading the light from said observing light source onto the object, said measuring light projecting means comprises a measuring light source lighted at predetermined intervals whenever said observing light source goes out, a light guide leading the light from said measuring light source onto the object and a grate pattern arranged in front of the exit end of said light guide and said image pickup optical system comprises a solid-state image sensor and a color encoding filter arranged in front of said solid-state image sensor.

8. A measuring endoscope according to claim 1 wherein said observing light projecting means and measuring light projecting means comprise a common light source, a common light guide leading the light from said light source onto the object, a pair of filters arranged movably as connected with each other between said light source and the entrance end of the light guide and making only the visible light and infrared light from said light source alternately incident upon the entrance end of said light guide and a measuring pattern arranged in front of the exit end of said light guide and said image pickup optical system comprises a solid-state image sensor and a color encoding mosaic filter arranged in front of said solid-state image sensor.

* * * * *